US00PP09822P

United States Patent [19]

Spira et al.

[11] Patent Number: Plant 9,822

[45] Date of Patent: Mar. 11, 1997

[54] ASIAN PEAR TREE NAMED 'ASIO 4'

[75] Inventors: Joel S. Spira; Ruth R. Spira, both of Coopersburg; Eugene S. Konno, Germansville; Neil J. Vincent, Quakertown, all of Pa.

[73] Assignee: Subarashii Kudamono Co., Inc., Coopersburg, Pa.

[21] Appl. No.: 538,201

[22] Filed: Oct. 8, 1995

[51] Int. Cl.[6] ..... A01H 5/00

[52] U.S. Cl. ..... Plt./36

[58] Field of Search ..... Plt./36

*Primary Examiner*—James R. Feyrer

*Attorney, Agent, or Firm*—Burns, Doane, Swecker & Mathis

[57] ABSTRACT

A new and distinct variety of Asian Pear, botanically known as *Pyrus pyrifolia* is provided. The new cultivar forms attractive late-season medium-sized ovate fruit having a light brown russet surface with prominent raised tan lenticels and a very sweet and rich flavor. The tree also exhibits a vigorous dense growth habit and is well branched. The leaves are medium green in coloration with pinnate finely-branched venation and an acuminate apex. The picking of the fruit commonly occurs during mid- to late-October at Coopersburg, Pa., U.S.A. Substantial and consistent fruit crops are formed.

3 Drawing Sheets

SUMMARY OF THE INVENTION

The present invention comprises a new and distinct cultivar of Asian Pear, botanically known as *Pyrus pyrifolia,* and hereinafter is referred to by the cultivar name 'Asio 4'.

The new cultivar germinated from a seed as a distinctive seedling during the summer of 1983 while growing in a test orchard at 1506 Pleasant View Road, Coopersburg, Pa., U.S.A. The new cultivar was discovered among hundreds of seedlings that were produced for test purposes. The seed that produced the new cultivar of the present cultivar was obtained from Japan and was formed on open-pollinated Asian Pear trees. It is impossible to further identify the parent plants of the new cultivar. A single tree of the new cultivar was discovered in the test orchard following selective study and initially was designated No. 919.

Since the summer of 1987 the original tree of the new cultivar has annually produced a crop of high quality Asian Pears.

It was found that the new 'Asio 4' cultivar of the present invention:

(a) forms attractive late-season medium-sized ovate fruit having a light brown russet surface with prominent tan lenticels and a very sweet and rich flavor,
(b) forms a large-sized tree having a well-branched, dense, and spreading growth habit, and
(c) forms generally elliptical medium-sized green leaves with pinnate venation and an acuminate apex.

It was found that the new 'Asio 4' cultivar flowers substantially concurrently with the 'Seuri' cultivar (non-patented in the United States), but matures a few days later than the 'Seuri' cultivar. The fruit of the 'Asio 4' cultivar possesses a prominent calyx-end lobe unlike the 'Seuri' cultivar and exhibits a lighter brown skin coloration. Also, the fruit flavor of the 'Asio 4' cultivar is sweeter and more intense than that of the 'Seuri' cultivar.

Asexual reproduction of the new cultivar by budding on 'Bartlett' rootstock carried out at Aspers, Pa., U.S.A., beginning during 1987, has demonstrated that the characteristics of the new cultivar as herein disclosed are firmly fixed and are retained through successive generations of such asexual propagation.

'Asio 4' has not been observed under all possible environmental conditions to date. Accordingly, it is possible that the phenotype may vary somewhat with variations in the environment, such as temperature, light, day length, contact with pesticides, etc.

It is contemplated that 'Asio 4' will be marketed under the SuSan trademark.

BRIEF DESCRIPTION OF THE PHOTOGRAPHS

The accompanying photographs show in color as nearly true as it is reasonably possible to make the same in color illustrations of this character the original tree of the new variety as well as plant parts thereof. The spreading tree was approximately 11 years of age and was growing on its own roots at 1506 Pleasant View Road, Coopersburg, Pa., U.S.A. All photographs with the exception of FIG. 2 and FIG. 6 were taken on Sep. 14, 1994.

Figure 3:
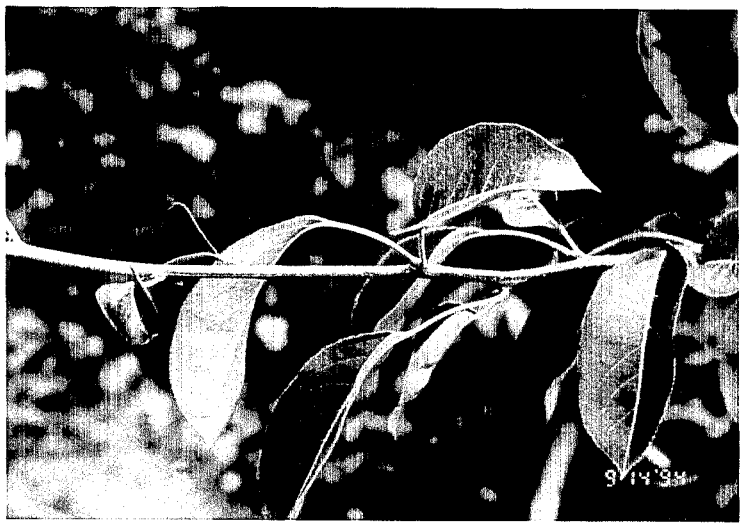

FIG. 3 illustrates a typical limb of the new cultivar wherein the generally elliptical leaves with fine serrated edges are apparent. A single leaf commonly appears at each node. While two leaves may appear to be present at a single node in the photograph, this is not what actually occurs. More specifically, where two leaves appear to originate from nearby locations in the photograph, this is believed to be the result of an additional extremely small spur or an unusually compressed internode spacing. Such leaf placement is exhibited in a number of Asian Pear cultivars and is not necessarily considered to be a distinguishing charcteristic of 'Asio 4'.

Figure 4:
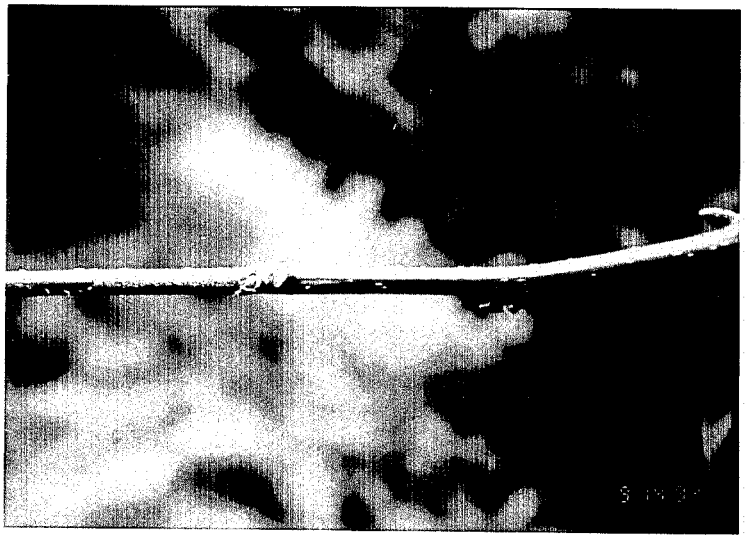

FIG. 4 illustrates a typical limb of the new cultivar wherein the leaves have been removed so that the appearance of the limb is totally unobstructed and the lenticels clearly are visible.

Figure 5:
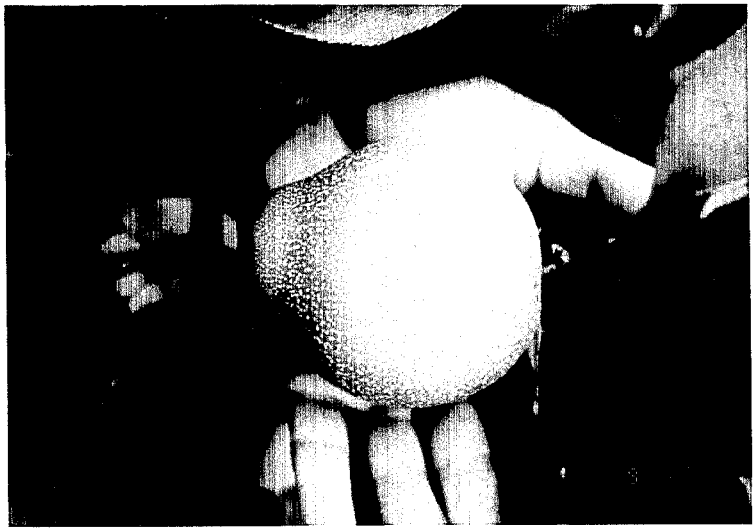

FIG. 5 illustrates a specimen of a medium-sized ovate fruit having prominent lenticels while present on the tree. Such fruit became ready for harvest approximately one month later and its surface darkened somewhat in coloration prior to the time of harvest.

Figure 6:
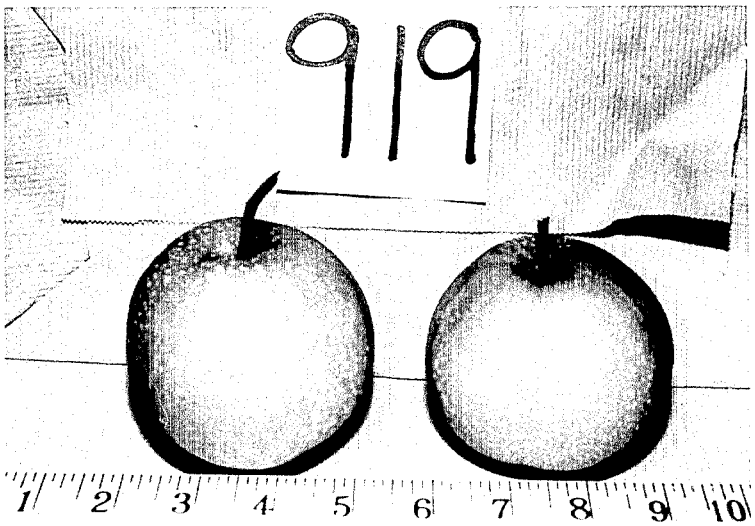

FIG. 6 illustrates additional specimens of the fruit of the new cultivar that were harvested during mid-October, 1994, placed in refrigerated storage at approximately 32° F., removed from such storage, and photographed on Dec. 4, 1994. Some of the darkening of the fruit seen in the photograph is attributable to the extended period of cold storage. As illustrated, the ovate fruit configuration of the new variety is somewhat variable with the fruit of FIG. 5 being somewhat more clubbed than that displayed in FIG. 6. A measuring stick in inches is provided at the bottom of the photograph for comparative purposes.

DETAILED DESCRIPTION

The chart used in the identification of the colors described hereafter is The R.H.S. Colour Chart of The Royal Horticultural Society, London, England. In some instances common color terms are used which are to be accorded their ordinary dictionary significance. The trees described were being grown under standard orchard conditions at Coopersburg, Pa., U.S.A.

Classification:

*Botanical.*—*Pyrus pyrifolia* (*P. serotina*), cv. 'Asio 4'.

*Commercial.*—Asian Pear.

Tree:

*Size.*—Large. The original tree at the age of 12 years is approximately 16 feet tall. Three years following the field planting of a tree that was budded 1½ years earlier on 'Barlett' rootstock, a tree height of approximately 6 feet commonly will be observed. Five years following field planting of a tree that was budded 1½ earlier on 'Bartlett' rootstock, a tree height of approximately 10 feet commonly will be observed.

*Growth habit.*—Vigorous.

*Configuration*—Spreading.

*Density.*—Very dense and well-branched. There commonly is more leaf mass per unit of tree volume than is exhibited by typical Asian Pear cultivars. This allows for good limb selection and spacing.

*Hardiness.*—Hardy in wood and bud.

*Fruit bearing.*—Productive.

*Bearing habit.*—Annually on second-year and older wood with the fruit being borne laterally and terminally on second year and older shoots, as well as laterally on spurs.

Figure 1:
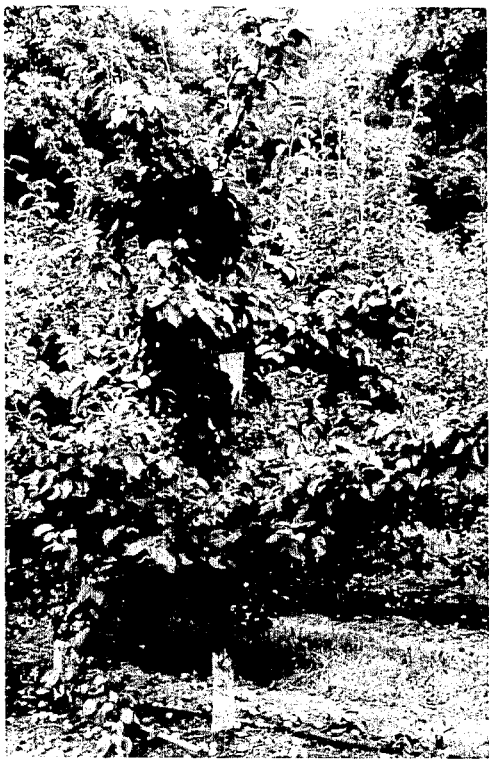
FIG. 1 illustrates the entire tree of the new cultivar wherein the large tree size and the dense well-branched, spreading, and vigorous growth habit are apparent. The fruit shown on the ground was removed by thinning in accordance with standard practice during the growing of Asian Pears in order to maximize fruit size.

*Trunk.*—Medium diameter and textured (as illustrated in FIG. 1).

*Branches.*—Thickness: medium. Bark texture: smooth (as illustrated). Frequency: moderate branching. Branch angles: the angles of the main scaffold branches commonly are approximately 60 degrees under natural growing conditions. When limb spreaders are employed, branch angles of approximately 90 degress can be achieved thereby resulting in earlier fruit bearing. Bark color: medium greenish-brown on younger wood. Lenticles: numerous, prominent, and tan in coloration (as illustrated).

Figure 2:
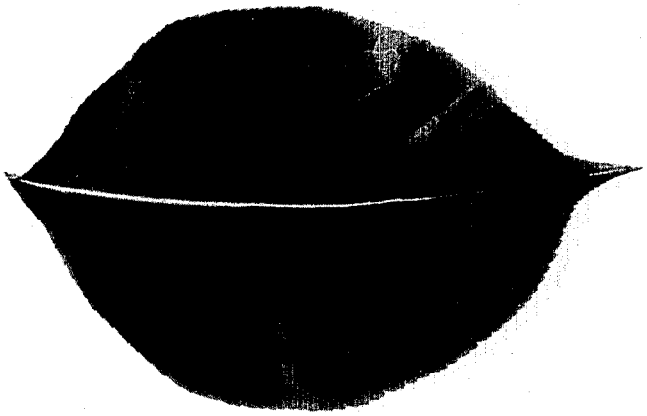
FIG. 2 illustrates a typical generally elliptical leaflet of the new cultivar wherein the fine serration pattern, pinnate venation with many small branches, and acuminate apex are more readily apparent. This photograph was prepared on Aug. 26, 1995.

*Leaves.*—Size: medium, commonly approximately 4 inches in length on average. Configuration: elliptical. Base: rounded. Apex: accuminate. Margin: finely serrulate (as illustrated in FIG. 2). Venation: pinnate with many fine branches. Thickness: medium. Color upper surface: during a typical growing season commonly approximates Green Group 135A, and during the fall is purplish which begins interveinally as Greyed-Purple Group 187B. Color under surface: during a typical growing season is silvery green, Green Group 137D, and during the fall initially tends to remain green as fall coloration develops on the upper surface and subsequently changes to the fall coloration, as illustrated in FIG. 3. Petiole: medium in length, and commonly approximately 1.4 inch in length.

*Flowers.*—Season: mid-season, and generally concurrent with the 'Seuri' cultivar. During 1993, the first bud break occurred on April 16th, and full bloom occurred on May 1st. During 1994, the first bud break occurred on April 15th, and full bloom occurred on April 26th. The flowering season also commonly approximates that of our 'Asio 3' cultivar (U.S. Plant Pat. application Ser. No. 08/531,184, filed Sep. 15, 1995). Size: medium, and commonly approximately 1.3 inches in diameter on average. Color: white, White Group 155A. Pollen: viable pollen is produced which has enabled 'Asio 4' to be utilizes as a pollen parent in interspecific crosses that have been carried out annually since 1988. When attempts have been made to self-pollinate 'Asio 4', no resulting fruit has set to date. Accordingly, the preliminary indications are that 'Asio 4' may be self-infertile. Bearing: commonly in corymb of 6 to 8 flowers. Configuration: the reproductive organs are similar to those of the species. The flowers generally possess five pistils and bear fruit having five sets of carpels.

*Fruit.*—Season of maturity: late season, maturing a few days later than the 'Seuri' cultivar. During 1993, the first picking was on October 10th and the last picking was on November 1St. During 1994, the first picking was on October 10th, and the last picking was on October 21st. Bearing: most of the fruit is borne laterally on spurs; however, some fruit also can be produced laterally on shoots. Size: medium to large, and commonly approximately 2.4 to 3.2 inches in diameter. The fruit weight commonly ranges from approximately 150 to 250 grams. It is recommended that the fruit be thinned in order to encourage the formation of the larger-sized fruit within the specified range. Configuration: ovate, commonly possesses a prominent lobe at the calyx end, and is somewhat variable in shape as illustrated in FIGS. 5 and 6. Such a pronounced lobe at the calyx end is absent in the 'Seuri' cultivar. Neck: as illustrated in FIGS. 5 and 6. Stem: medium in length, clubbed, and with many prominent lenticels. Cavity: acute. Basin: narrow. Calyx: divergent and persistent. Skin: light green ground cover with a complete light brown russet surface and numerous prominent raised tan lenticels (as illustrated). The russet surface of the new variety commonly is a lighter brown than that of the 'Seuri' cultivar. The skin commonly is near Greyed-Orange Group 164A, and the lenticels commonly are Greyed-Orange Group 165D. A distinctive ring of Yellow-Green Group 144A commonly is present on the lobe of the calyx end. Flesh: juicy, crisp, and white. The texture is similar to that of the 'Seuri' cultivar. Flavor: very sweet (TSS 13 to 14 Brix), and very rich with low acid. The distinctive fruit flavor is unlike the almost banana flavor of the 'Seuri' cultivar, and is sweeter and more intense that than the flavor of the 'Seuri' cultivar. The flesh of 'Asio 4' tends to be somewhat less sweet and drier near the core than elsewhere. Core: median. Carpels: roundish, with axial symmetry. Seeds: commonly 6 to 10 per fruit, commonly 1 or 2 per carpel, medium-sized, commonly flattened on one side, and dark brown in coloration. Quality: very good. Keeping quality: very good, can be stored at least 2 months in good condition at 32° F. The storage life of the new cultivar is generally longer than that of the 'Seuri' cultivar. Fire blight resistance: no inoculations for fire blight screening have been carried out; however, it is believed that at least some resistance to fire blight is being exhibited. For instance, when fire blight strikes have occurred in the orchard where 'Asio 4' was being grown, no fire blight has been observed in 'Asio 4'.

We claim:

1. A new and distinct cultivar of Asian Pear, substantially as illustrated and described, which:

(a) forms attractive late-season medium-sized ovate fruit having a light brown russet surface with prominent tan lenticles and a very sweet and rich flavor, (b) forms a large-sized tree having a well-branched, dense, and spreading growth habit, and (c) forms generally elliptical medium-sized green leaves with pinnate venation and an acuminate apex.

* * * * *